(12) United States Patent
Lawrence et al.

(10) Patent No.: US 6,548,523 B2
(45) Date of Patent: Apr. 15, 2003

(54) PROCESS FOR THE PREPARATION OF ARYLETHANOLAMINE DERIVATIVES HAVING AN ANTI-OBESITY AND ANTI-DIABETIC PROPERTIES

(75) Inventors: Ronnie Maxwell Lawrence, Stevenage (GB); Alan Millar, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/148,841
(22) PCT Filed: Dec. 8, 2000
(86) PCT No.: PCT/GB00/04697
§ 371 (c)(1), (2), (4) Date: Jun. 4, 2002
(87) PCT Pub. No.: WO01/42195
PCT Pub. Date: Jun. 14, 2001

(65) Prior Publication Data
US 2002/0198220 A1 Dec. 26, 2002

(30) Foreign Application Priority Data
Dec. 11, 1999 (GB) ................................ 9929297

(51) Int. Cl.[7] ................ C07D 213/80; C07C 237/06; A61K 31/44
(52) U.S. Cl. ............. 514/357; 514/256; 514/342; 514/365; 514/626; 514/646; 544/333; 544/335; 546/264; 546/269.7; 546/334; 546/336; 548/203; 564/194; 564/203
(58) Field of Search ................. 544/333, 335; 546/264, 269.7, 334, 336; 548/203; 564/194, 203; 514/256, 342, 357, 365, 626, 646

(56) References Cited
FOREIGN PATENT DOCUMENTS

| EP | 0 543 662 | 5/1993 |
| GB | 1 551 260 | 8/1979 |
| WO | 97/21666 | 6/1997 |

OTHER PUBLICATIONS

Hu Y, J. et al., "H–phosphate derivatives as novel peptide deformylase inhibitors," *Bioorganic & Medicinal Chemistry Letters*, vol. 8, No. 18, Sep. 22, 1998, pp. 2479–2482.

Hajduk, Philip J. et al., "NMR–based discovery of lead inhibitors that block DNA binding of the human papillomavirus E2 protein," *Journal of Medicinal Chemistry*, vol. 40, No. 20, 1997, pp. 3144–3150.

*Primary Examiner*—Zinna Northington Davis
(74) *Attorney, Agent, or Firm*—Amy H. Fix

(57) ABSTRACT

The present invention is a process for the preparation of a compound of Formula (IA) or a pharmaceutically acceptable salt thereof:

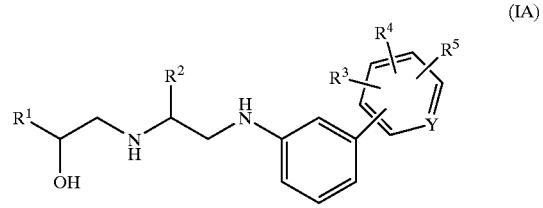

(IA)

that includes preparing a diamide of Formula (II) or a pharmaceutically acceptable salt thereof:

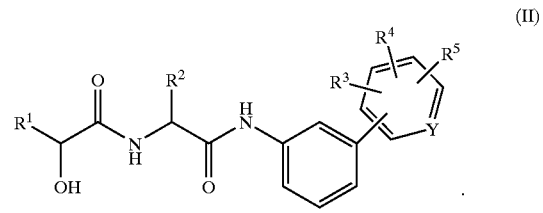

(II)

11 Claims, No Drawings

PROCESS FOR THE PREPARATION OF ARYLETHANOLAMINE DERIVATIVES HAVING AN ANTI-OBESITY AND ANTI-DIABETIC PROPERTIES

This application is filed pursuant to 35 U.S.C. §371 as a United States National Phase Application of International Application No. PCT/GB00/04697 filed Dec. 8, 2000, which claims priority from GB 9929297.1 filed Dec. 11, 1999

FIELD OF THE INVENTION

This invention relates to a method for the preparation of certain biaryl derivatives.

BACKGROUND OF THE INVENTION

Atypical beta-adrenoceptors are known to occur in adipose tissue and the gastrointestinal tract. Atypical beta-adrenoceptor agonists have been found to be particularly useful as thermogenic anti-obesity agents and as anti-diabetic agents. Compounds having a typical beta-adrenoceptor agonist activity have also been described as being useful in the treatment of hyperglycaemia, as animal growth promoters, as blood platelet aggregation inhibitors, as positive inotropic agents and as antiatherosclerotic agents, and as being useful in the treatment of glaucoma.

A UK patent application filed on Jun. 13, 1998 as GB 9812709.5 (and corresponding International patent application WO99/65877), discloses compounds of Formula (I) and pharmaceutically acceptable derivatives thereof:

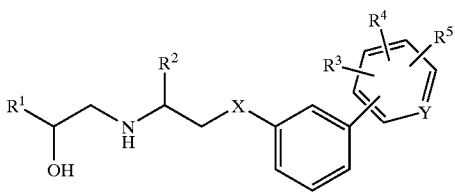

(I)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, nitro, cyano, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
X is oxygen, NH, or $NC_{1-4}$alkyl;
$R^3$ is cyano, tetrazol-5-yl, or $CO_2R^7$ where $R^7$ is hydrogen or $C_{1-6}$alkyl;
$R^4$ and $R^5$ are independently hydrogen, $C_{1-6}$alkyl, —$CO_2H$, —$CO_2C_{1-6}$alkyl, cyano, tetrazol-5-yl, halogen, trifluoromethyl, or $C_{1-6}$alkoxy, or, when $R^4$ and $R^5$ are bonded to adjacent carbon atoms,
$R^4$ and $R^5$ may, together with the carbon atoms to which they are bonded, form a fused 5 or 6 membered ring optionally containing one or two nitrogen, oxygen, or sulfur atoms; and
Y is N or CH.

SUMMARY OF THE INVENTION

Briefly, in one aspect, the present invention provides a process for the preparation of a compound of Formula (IA) or a pharmaceutically acceptable salt thereof:

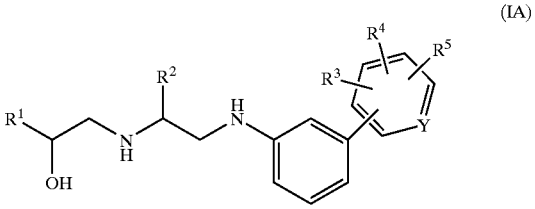

(IA)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
$R^3$ is $CO_2R^7$ where $R^7$ is hydrogen or $C_{1-6}$alkyl;
$R^4$ and $R^5$ are independently hydrogen, $C_{1-6}$alkyl, —$CO_2C_{1-6}$alkyl; and
Y is N or CH
comprising the step of preparing a diamide of Formula (II) or a pharmaceutically acceptable salt thereof:

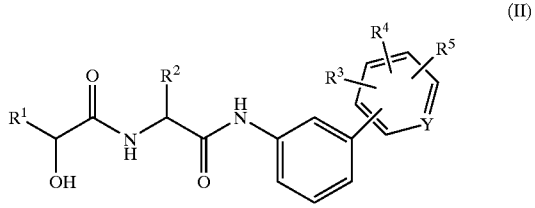

(II)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
$R^3$ is $CO_2R^7$ where $R^7$ is $C_{1-6}$alkyl;
$R^4$ and $R^5$ are independently hydrogen, $C_{1-6}$alkyl, —$CO_2C_{1-6}$alkyl; and
Y is N or CH.

In an alternative aspect, the invention provides a process for the preparation of a compound of Formula (IA):

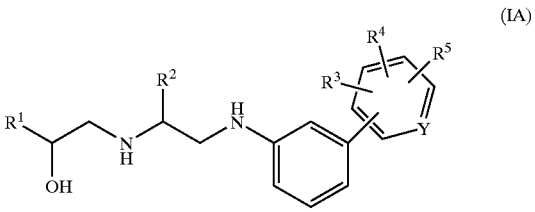

(IA)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
$R^3$ is $CO_2R^7$ where $R^7$ is hydrogen or $C_{1-6}$alkyl;
$R^4$ and $R^5$ are independently hydrogen, $C_{1-6}$alkyl, —$CO_2C_{1-6}$alkyl; and Y is N or CH, or a pharmaceutically acceptable salt thereof, comprising reduction of a compound of Formula (II):

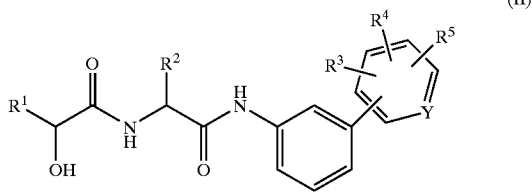

(II)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
$R^3$ is $CO_2R^7$ where $R^7$ is $C_{1-6}$alkyl;
$R^4$ and $R^5$ are independently hydrogen, $C_{1-6}$alkyl, —$CO_2C_{1-6}$alkyl; and
Y is N or CH, or a pharmaceutically acceptable salt thereof, and optionally the step of hydrolysis of the resulting ester group $R^7$ in Formula (IA) to produce a compound of Formula (IA) wherein $R^7$ is H.

In another aspect, the present invention provides a compound of Formula (II), wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;
$R^2$ is hydrogen or $C_{1-6}$alkyl;
$R^3$ is $CO_2R^7$ where $R^7$ is $C_{1-6}$alkyl;
$R^4$ and $R^5$ are independently hydrogen, $C_{1-6}$alkyl, —$CO_2C_{1-6}$alkyl; and
Y is N or CH, or a pharmaceutically acceptable salt thereof.

DETAILED DESCRIPTION OF THE INVENTION

As used herein, the terms "alkyl" and "alkoxy" mean a straight or branched alkyl group or alkoxy group respectively, containing the indicated number of carbon atoms. For example, $C_{1-6}$alkyl means a straight or branched alkyl containing at least 1 and at most 6 carbon atoms.

As used herein, the term "aryl" means monocyclic or bicyclic aromatic carbocyclic groups such as phenyl and naphthyl.

Preferably, $R^1$ is phenoxymethyl or phenyl optionally substituted by one, two or three substituents selected from halogen, hydroxy, $C_{1-6}$alkoxy, $C_{1-6}$alkyl, hydroxymethyl and trifluoromethyl. More preferably, $R^1$ is phenoxymethyl or phenyl substituted by a chlorine, fluorine or bromine atom or a methyl or trifluoromethyl group, which atom or group is preferably located in the meta position. Most preferably $R^1$ is phenyl substituted by a chlorine atom located in the meta position.

Preferably, $R^2$ is hydrogen or methyl. Most preferably $R^2$ is hydrogen.

Preferably, $R^3$ is bonded to the carbon atom meta to the bonded phenyl ring. In a compound of Formula (IA), $R^3$ is preferably $CO_2H$. In a compound of Formula (II), $R^3$ is preferably $CO_2CH_3$.

Preferably, at least one of $R^4$ and $R^5$ is hydrogen. Most preferably, both $R^4$ and $R^5$ are hydrogen.

Preferably Y is CH.

Particularly preferred compounds, or compounds of the processes, of the invention include those in which each variable is selected from the preferred groups for each variable. Even more preferable compounds of the invention include those where each variable is selected from the more preferred or most preferred groups for each variable.

Reagents for the transformation of a compound of Formula (II) to a compound of Formula (I) include any suitable reagent for the reduction of amide carbonyl bonds, e.g. borane-ether, borane-sulfide, borane-amine complexes and also conditions which form borane in situ (for example, sodium borohydride and iodine or sulfuric acid). Suitable solvents include hydrocarbons, e.g. toluene or ethers, e.g. tetrahydrofuran. The reaction may be conveniently carried out on a solid substrate, such as a bead or standard substrate used in solid-phase synthesis. For example, a compound of Formula (II) may be attached to the solid substrate through the group $R^3$, i.e. —$CO_2$-solid substrate.

In order to form a compound of Formula (IA) wherein $R^7$ is hydrogen, the step of reduction of a compound of Formula (II) should be followed by hydrolysis of the resulting ester group $R^7$.

A compound of Formula (II) may be prepared by reaction of a compound of Formula (III) with a compound of Formula (IV)

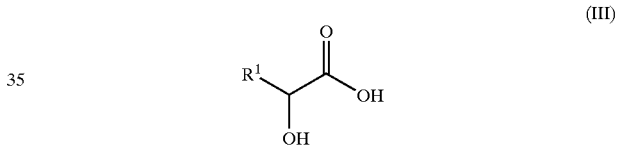

(III)

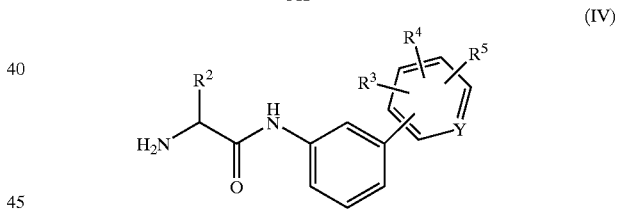

(IV)

using any suitable method for forming an amide link, e.g. suitable coupling agents include diimides, e.g. diisopropylcarbodiimide, dicyclohexylcarbodiimide, or carbonyl diimidazole, hydroxytriazoles and equivalents, or chloroformates, whilst suitable solvents include esters, e.g. ethyl acetate, ethers, halogenated solvents, N-methylpyrrolidinone, acetonitrile or trifluorobenzene.

As a further aspect of the present invention, there is provided a compound of Formula (IV), wherein $R^2$ is hydrogen or $C_{1-6}$alkyl; $R^3$ is $CO_2R^7$ where $R^7$ is $C_{1-6}$alkyl; $R^4$ and $R^5$ are independently hydrogen, $C_{1-6}$alkyl, —$CO_2C_{1-6}$alkyl; and Y is N or CH, or a pharmaceutically acceptable salt thereof.

Compounds of Formula (III) are commercially available or may be prepared by standard methods, for example, as described in the examples herein.

Compounds of Formula (IV) may be prepared from compounds of Formula (V)

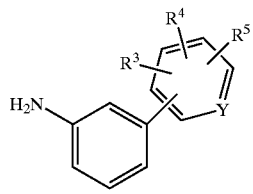

(V)

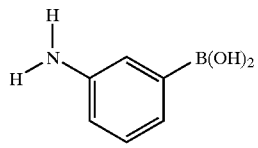

(IX)

using any suitable method for forming an amide link. For example, a compound of Formula (V) may be treated with a compound of Formula (VIII)

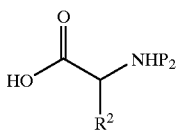

(VIII)

using standard coupling procedures, e.g. diimide coupling agents, e.g. diisopropylcarbodiimide, dicyclohexylcarbodiimide or carbonyl diimidazole with a suitable glycine compound, e.g. N-Boc-glycine, in a suitable solvent such as esters, e.g. ethyl acetate, ethers, or hydrocarbons. $P_2$ is a standard protecting group for a nitrogen, for example butoxy carbonyl.

Compounds of Formula (V) may be prepared by reaction of a compound of Formula (VI) with a compound of Formula (VII) according to the method of Thompson, (*J. Org. Chem.* 1984, 49, 5237),

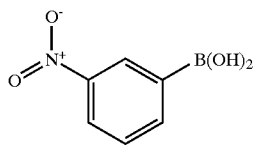

(VI)

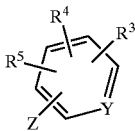

(VII)

where Z is halogen or triflate, using a suitable boronic acid coupling conditions, e.g. palladium on carbon and sodium carbonate or $Pd(PPh_3)_4$ (tetrakis(triphenylphosphine) palladium (0)), followed by reduction of the nitro group using standard methods, e.g. under hydrogen using a suitable catalyst, such as palladium on carbon, in a suitable solvent such as an alcohol, tetrahydrofuran, DME, ethyl acetate, toluene, iso-octane, cyclohexane or water or mixtures thereof, optionally at elevated temperature.

Compounds of Formula (IV) may also be conveniently prepared using a two step one-pot reaction starting from reaction of a compound of Formula (VI) with a compound of Formula (VII) under conditions described above, i.e. in the presence of a palladium on carbon catalyst, followed by reduction of the nitro group under hydrogen, using the reagents described above.

Compounds of Formula (V) may also be prepared by reaction of a compound of Formula (VII) with a compound of Formula (IX) using standard boronic acid coupling methods described above.

EXAMPLES

The invention is further illustrated by the following intermediates and examples. All temperatures are in degrees centigrade. Mass spectra (ms) were obtained using electrospray (positive or negative ion) analysis.

Methyl 3'-amino[1,1'-biphenyl]-3-carboxylate

Method 1

A mixture of 3-nitrobenzeneboronic acid (20 g), methyl 3-bromobenzoate (27 g), sodium carbonate (14 g) and 10% palladium on carbon (50% wet paste, 1 g) in methanol (120 ml) was heated under reflux for 2 hours. The mixture was taken off reflux, diluted with iso-propyl acetate (240 ml) and cooled to room temperature. The mixture is stirred under an atmosphere of hydrogen until uptake ceases, water (80 ml) is added and the suspension is filtered. The filtrate is separated and the organic phase is washed with brine. The organic solution is concentrated by distillation to a low volume, treated with cyclohexane and filtered to give the title compound as a beige solid (24.5 g).

Mass spec. M+H=228 (electrospray).

Method 2

A mixture of 3-aminophenylboronic acid hemisulfate (0.5 g), methyl 3-bromobenzoate (0.61 g), sodium carbonate (0.57 g) and 10% palladium on carbon (50% wet paste, 30 mg) in methanol (5.4 ml) was heated under reflux for 14 hours. The mixture was taken off reflux, diluted with ethyl acetate (20 ml) and filtered through a Celite pad, rinsing through with ethyl acetate. The filtrate was washed with water (10 ml) and saturated brine (10 ml). The organic phase was dried over sodium sulfate and concentrated in vacuo to give the title compound as a dark oil, which slowly solidifies (0.58 g).

Methyl 3'-amino[1,1'-biphenyl]-3-carboxylate hydrochloride

A mixture of 3-nitrobenzeneboronic acid (20 g), methyl 3-bromobenzoate (27 g), sodium carbonate (14 g) and 10% palladium on carbon (50% wet paste, 1 g) in methanol (120 ml) was heated under reflux for 2 hours. The mixture was taken off reflux, diluted with iso-propyl acetate (240 ml) and cooled to room temperature. The mixture is stirred under an atmosphere of hydrogen until uptake ceases, water (80 ml) is added and the suspension is filtered. The filtrate is separated and the organic phase is washed with brine. The organic solution is concentrated by distillation and treated with anhydrous hydrochloric acid (prepared from acetyl chloride (19 ml) and isopropanol (82 ml)) to give the title compound as a white solid (29.5 g).

Methyl 3'-[(aminoacetyl)amino][1,1'-biphenyl]-3-carboxylate hydrochloride

Method 1

A mixture of methyl 3'-amino[1,1'-biphenyl]-3-carboxylate (4.0 g), N-tert-butoxycarbonylglycine (3.24 g) and dicyclocarbodiimide (3.81 g) in ethyl acetate (48 ml) was stirred at room temperature for 1 hour, cooled to 5° C. and filtered. The solid was washed with ethyl acetate (8 ml) and the combined organic layers were washed with aqueous sodium bicarbonate and then water. The organic solution is treated with concentrated hydrochloric acid (3.5 ml), stirred overnight and the mixture is filtered to give the title compound as a white solid (4.4 g).

$^1$H NMR (400 MHz, DMSO) δ ppm: 3.84(s broad); 3.90 (s); 7.45 (ddd); 7.49 (dd); 7.66 (dd); 7.68 (ddd); 7.93 (ddd); 7.98 (ddd); 8.00 (dd); 8.17 (dd); 8.32(broad peak); 10.97 (s).

Method 2

A mixture of 3-nitrobenzeneboronic acid (20 g), methyl 3-bromobenzoate (27 g), sodium carbonate (14 g) and 10% palladium on carton (50% wet paste, 1 g) in methanol (120 ml) was heated under reflux for 2 hours. The mixture was taken off reflux, and diluted with iso-propyl acetate (240 ml) and cooled to room temperature. The mixture is stirred under an atmosphere of hydrogen until uptake ceases, water (80 ml) is added and the suspension is filtered. The filtrate is separated and the organic phase is washed with brine. The organic solution is concentrated by distillation to a low volume, cooled to room temperature and then treated sequentially with N-tert-butoxycarbonylglycine (21 g) and 1,3-diisopropylcarbodiimide (19 ml) at less than 30° C. The mixture is stirred for 1 hour, filtered and the solid is washed with further iso-propyl acetate. The combined filtrates are washed with 2M aqueous sodium carbonate and then water. The organic solution is treated with concentrated hydrochloric acid (35 ml), stirred overnight and the mixture is filtered to give the title compound as a white solid (33 g).

Methyl 3'-[({[(2S)-2-(3-chlorophenyl)-2-hydroxyethanoyl]amino}acetyl)amino][1,1'-biphenyl]-3-carboxylate A suspension of methyl 3'-[(aminoacetyl)amino][1,1'-biphenyl]-3-carboxylate hydrochloride (50 g) in ethyl acetate (350 ml) is treated with 1 M aqueous sodium carbonate (250 ml) at room temperature. The lower aqueous phase is discarded, 1-hydroxybenzotriazole hydrate (10 g) and then dicyclohexylcarbodiimide (30.6 g) is added to the organic phase and the mixture is cooled to approximately 10° C. This mixture is treated with a solution of (R)-3-chloromandelic acid (5.8 g) in ethyl acetate (40 ml) over approximately 1 hour. The mixture is stirred for several hours and filtered. The filtrate is washed with 6% w/w aqueous sodium bicarbonate and water, and the organic phase is concentrated to low volume. Isopropanol is added and the organic solution is further concentrated to low volume. The organic solution is warmed to 70° C., treated with water, cooled to room temperature and the mixture is filtered to give the title product (60 g).

Mass spec. M+H=453/455 (electrospray).

Methyl 3'-[(2-{[(2R)-2-(3-chlorophenyl)-2-hydroxyethyl]amino}ethyl)amino][1,1'-biphenyl]-3-carboxylate hydrochloride Method 1

A solution of methyl 3'-[({[(2S)-2-(3-chlorophenyl)-2-hydroxyethanoyl]amino}acetyl)amino][1,1'-biphenyl]-3-carboxylate (10 g) in tetrahydrofuran (40 ml) is heated to 40–60° C. and treated with a solution of 1 M borane-tetrahydrofuran complex in tetrahydrofuran (51 ml) over 15–60 minutes. The mixture is heated at this temperature for approximately 2 hours, then treated with further of 1 M borane-tetrahydrofuran complex in tetrahydrofuran (6.7 ml). After approximately 2 hours further, 1 M borane-tetrahydrofuran complex in tetrahydrofuran (4.4 ml) is added. The reaction is stirred overnight at this temperature, and then methanol (13 ml) is added. A solution of anhydrous hydrogen chloride (prepared from acetyl chloride (4.7 ml) and methanol (50 ml) is added to the mixture, and the resulting suspension is concentrated to low volume, diluted with ethyl acetate, cooled to 0–5° C. and filtered to give the title compound as a white solid (8.2 g).

Method 2

A suspension of methyl 3'-[({[(2S)-2-(3chlorophenyl)-2-hydroxyethanoyl]amino}acetyl)amino][1,1'-biphenyl]-3-carboxylate (10 g) in toluene (44 ml) is heated to 100° C. and treated with a solution of borane-dimethylsulfide complex (4.9 ml) over 60–120 minutes. The mixture is heated for a further 1–4 h, cooled and treated with ethanol (44 ml). Concentrated hydrochloric acid (5.6 ml) is added, the suspension is stirred for 2–20 hours and filtered to give the title compound as a white solid (6.6 g).

Mass spec. M+H=425/427 (electrospray).

3'-[(2-{[(2R)-2-(3-chlorophenyl)-2-hydroxyethyl]amino}ethyl)amino][1,1'-biphenyl]-3-carboxylic acid hydrochloride A suspension of methyl 3'-[(2-{[(2R)-2-(3-chlorophenyl)-2-hydroxyethyl]amino}ethyl)amino][1,1'-biphenyl]-3-carboxylate hydrochloride (10 g) and methanol (67 ml) at 40–50° C. is treated with 1.5N aqueous sodium hydroxide (60 ml) and held at this temperature for at least 1 hour. This solution is added to a solution of concentrated hydrochloric acid (10 ml) in water (20 ml) and methanol (33 ml) at 50° C. The resulting suspension is cooled to room temperature and filtered to give the title compound (8 g).

Mass spec. M+H=411/413 (electrospray).

$^1$H NMR (400 MHz, DMSO) δ ppm: 3.06 (dd); 3.17 (t); 3.25 (dd); 3.52 (t); 5.07 (d); 6.10(broad peak); 6.36(broad peak); 6.70 (dd); 6.89 (d); 6.92 (s); 7.23 (dd); 7.38 (m, broad); 7.47 (s); 7.57 (dd); 7.86 (d); 7.92 (d); 8.14 (s); 9.03(broad peak); 9.41(1 broad peak); 13.04(broad peak).

What is claimed is:

1. A process for preparation of a compound of Formula (IA) or a pharmaceutically acceptable salt thereof:

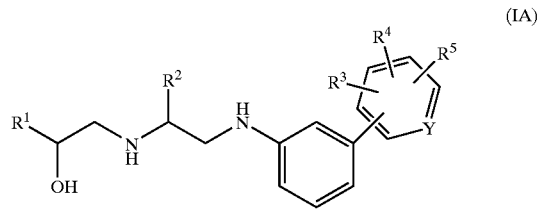

(IA)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;

$R^2$ is hydrogen or $C_{1-6}$alkyl;

$R^3$ is $CO_2R^7$ where $R^7$ is hydrogen or $C_{1-6}$alkyl;

$R^4$ and $R^5$ are independently hydrogen, $C_{1-6}$alkyl, or —$CO_2C_{1-6}$alkyl; and Y is N or OH comprising the step of preparing a diamide of Formula (II) or a pharmaceutically acceptable salt thereof:

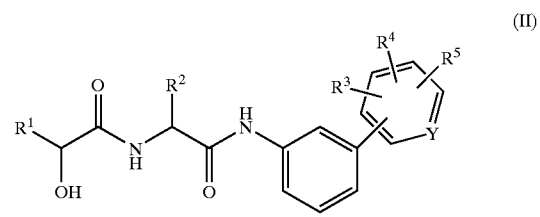

(II)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;

$R^2$ is hydrogen or $C_{1-6}$alkyl;

$R^3$ is $CO_2R^7$ where $R^7$ is $C_{1-6}$alkyl;

$R^4$ and $R^5$ are independently hydrogen, $C_{1-6}$alkyl, or —$CO_2C_{1-6}$alkyl; and Y is N or CH.

2. A process for the preparation of a compound of Formula (IA):

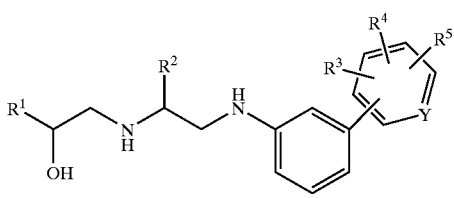

(IA)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;

$R^2$ is hydrogen or $C_{1-6}$alkyl;

$R^3$ is $CO_2R^7$ where $R^7$ is hydrogen or $C_{1-6}$alkyl;

$R^4$ and $R^5$ are independently hydrogen, $C_{1-6}$alkyl, or —$CO_2C_{1-6}$alkyl; and Y is N or CH, or a pharmaceutically acceptable salt thereof, comprising reduction of a compound of Formula (II):

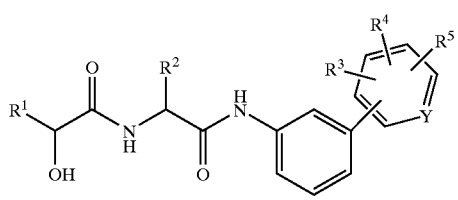

(II)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;

$R^2$ is hydrogen or $C_{1-6}$alkyl;

$R^3$ is $CO_2R^7$ where $R^7$ is $C_{1-6}$alkyl;

$R^4$ and $R^5$ are independently hydrogen, $C_{1-6}$alkyl, or —$CO_2C_{1-6}$alkyl; and Y is N or CH, or a pharmaceutically acceptable salt thereof, and optionally the step of hydrolysis of the resulting ester group $R^7$ in Formula (IA) to produce a compound of Formula (IA) wherein $R^7$ is H.

3. The process as claimed in claim 1 wherein $R^1$ represents phenyoxymethyl or phenyl optionally substituted by one, two or three substituents selected from halogen, hydroxy, $C_{1-6}$alkoxy, $C_{1-6}$alkyl, hydroxymethyl, and trifluoromethyl.

4. The process as claimed in claim 3 wherein $R^1$ represents phenoxymethyl or phenyl substituted by a chlorine, fluorine or bromine atom or a methyl or trifluoromethyl group.

5. The process as claimed in claim 1 wherein $R^2$ is hydrogen or methyl.

6. A process as claimed in claim 1 wherein at least one of $R^4$ and $R^5$ is hydrogen.

7. The process of claim 1 wherein said compound of Formula (IA) is selected from the group consisting of:

(R)-5-[3-[[2-[[2-(3-chlorophenyl)-2-hydroxyethyl] amino]ethyl]amino]phenyl]-3-pyridinecarboxylic acid;

3'-[[2R-[[2-(3-chlorophenyl)-2R-hydroxyethyl]amino] propyl]amino]-[1,1'-biphenyl]-2,4-dicarboxylic acid;

(R)-3'-[[2-[(2-hydroxy-3-phenoxypropyl)amino]ethyl] amino-[1,1'-biphenyl]-3-carboxylic acid;

(R)-3'-[[2-[[2-(3-chlorophenyl)-2-hydroxyethyl]amino] ethyl]amino]-[1,1'-biphenyl]-2-methyl-5-carboxylic acid;

(R)-3'-[[2-[[2-(3-chlorophenyl)-2-hydroxyethyl]amino] ethyl]amino]-[1,1'-biphenyl]-3-carboxylic acid; and pharmaceutically acceptable salts thereof.

8. A compound of Formula (II) or a pharmaceutically acceptable salt thereof:

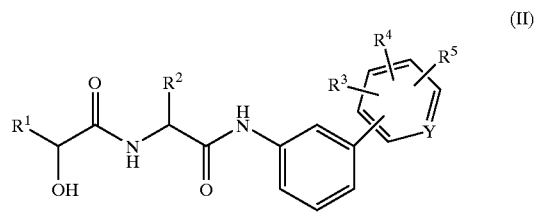

(II)

wherein $R^1$ is an aryl, pyridyl, thiazolyl, phenoxymethyl, or pyrimidyl group, optionally substituted by one or more substituents selected from the group consisting of halogen, hydroxy, $C_{1-6}$alkoxy, $C_{1-6}$alkyl, hydroxymethyl, trifluoromethyl, —$NR^6R^6$, and —$NHSO_2R^6$, where each $R^6$ is independently hydrogen or $C_{1-4}$alkyl;

$R^2$ is hydrogen or $C_{1-6}$alkyl;

$R^3$ is —$CO_2C_{1-6}$alkyl;

$R^4$ and $R^5$ are independently hydrogen, $C_{1-6}$alkyl, or —$CO_2C_{1-6}$alkyl; and Y is N or CH.

9. A process for the preparation of a compound of Formula (II) comprising reaction of a compound of Formula (III) with a compound of Formula (IV)

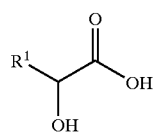

(III)

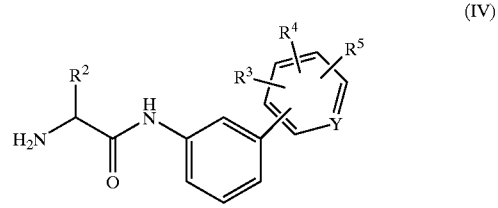

(IV)

10. A process as claimed in claim 9 which further comprises preparing a compound of Formula (IV) using a one-pot reaction in which a compound of Formula (IV) is reacted with a compound of Formula (VII) in the presence of a palladium on carbon catalyst and then reduced under hydrogen (VI)
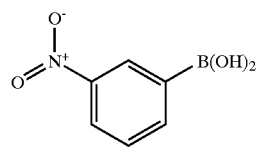
(VII)
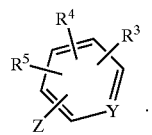
11. A compound of Formula (IV) or a pharmaceutically acceptable salt thereof:
(IV)
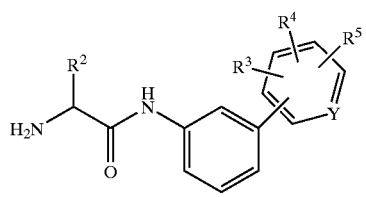
wherein:
  $R^2$ is hydrogen or $C_{1-6}$alkyl;
  $R^3$ is —$CO_2C_{1-6}$alkyl;
  $R^4$ and $R^5$ are independently hydrogen, $C_{1-6}$alkyl, or —$CO_2C_{1-6}$alkyl; and
  Y is N or CH.
* * * * *